(12) United States Patent
Daw et al.

(10) Patent No.: US 12,104,957 B2
(45) Date of Patent: Oct. 1, 2024

(54) IN-SITU INFRA-RED AND ULTRA-VIOLET PHOTOMETER

(71) Applicant: Protea Ltd, Middlewich (GB)

(72) Inventors: Chris Daw, Wing Oakham (GB); Robin Hutchinson, Deeping St. James (GB)

(73) Assignee: Protea Ltd, Middlewich (GB)

( * ) Notice: Subject to any disclaimer, the term of this patent is extended or adjusted under 35 U.S.C. 154(b) by 150 days.

(21) Appl. No.: 17/620,408

(22) PCT Filed: Jun. 25, 2020

(86) PCT No.: PCT/EP2020/067803
§ 371 (c)(1),
(2) Date: Dec. 17, 2021

(87) PCT Pub. No.: WO2020/260448
PCT Pub. Date: Dec. 30, 2020

(65) Prior Publication Data
US 2022/0341783 A1    Oct. 27, 2022

(30) Foreign Application Priority Data

Jun. 28, 2019 (GB) .................................... 1909290

(51) Int. Cl.
*G01J 3/427* (2006.01)
*G01J 3/02* (2006.01)
(Continued)

(52) U.S. Cl.
CPC ............. *G01J 3/427* (2013.01); *G01J 3/0218* (2013.01); *G01J 3/108* (2013.01); *G01J 3/12* (2013.01);
(Continued)

(58) Field of Classification Search
CPC .......... G01J 3/427; G01J 3/0218; G01J 3/108; G01J 3/12; G01J 2003/102;
(Continued)

(56) References Cited

U.S. PATENT DOCUMENTS 3,162,761 A    12/1964  Luft
3,999,062 A    12/1976  Demsky et al.
(Continued)

FOREIGN PATENT DOCUMENTS

CN    204405537 U    6/2015
CN    106168577 A    11/2016
(Continued)

*Primary Examiner* — David P Porta
*Assistant Examiner* — Mamadou Faye
(74) *Attorney, Agent, or Firm* — McCarter & English, LLP; James M. Smedley; Alex Korona

(57) ABSTRACT

The invention relates to a photometer (30) for analysing the composition of a sample gas. The photometer comprises an infra-red (IR) source (20) configured to direct a first plurality of pulses (40) of IR radiation through the sample gas to an IR detector (26), at least two of the first plurality of pulses being of different wavelength. The photometer further comprises an ultraviolet (UV) source (32) configured to generate a second plurality of pulses (38) of UV radiation for conveyance to a UV detector (36), at least two of the second plurality of pulses being of different wavelength. A path selection arrangement (22, 42-50) is configured to selectively convey different ones of the second plurality of pulses (38) to one of the sample gas and the UV detector (36). The photometer further comprises processing circuitry coupled to the IR source (20), the UV source (32), the IR detector (26), the UV detector (36) and the path selection arrangement (22, 42-50). The processing circuitry is configured to (i) select the wavelength to be used for a given UV pulse of the second plurality of pulses (38), (ii) receive a plurality of detection signals from each of the IR detector (26) and the
(Continued)

UV detector (36) and (iii) based on the detection signals, determine a concentration of at least one component of the sample gas. A method for analysing the composition of a sample gas is also disclosed.

18 Claims, 3 Drawing Sheets

(51) Int. Cl.
  *G01J 3/10* (2006.01)
  *G01J 3/12* (2006.01)
  *G01N 21/33* (2006.01)
  *G01N 21/3504* (2014.01)
  *G01N 33/00* (2006.01)
  *G01N 21/31* (2006.01)

(52) U.S. Cl.
  CPC ......... *G01N 21/33* (2013.01); *G01N 21/3504* (2013.01); *G01N 33/0037* (2013.01); *G01N 33/0042* (2013.01); *G01J 2003/102* (2013.01); *G01J 2003/1213* (2013.01); *G01N 2021/3155* (2013.01); *G01N 2201/08* (2013.01)

(58) Field of Classification Search
  CPC .... G01J 2003/1213; G01J 3/0232; G01J 3/10; G01J 3/42; G01N 21/33; G01N 21/3504; G01N 33/0037; G01N 33/0042; G01N 2021/3155; G01N 2201/08; G01N 1/2252; G01N 21/8507; G01N 21/3151
  See application file for complete search history.

(56) References Cited

U.S. PATENT DOCUMENTS

| | | | |
|---|---|---|---|
| 5,386,295 | A | 1/1995 | Switalski et al. |
| 6,841,778 | B1 | 1/2005 | Shifflett et al. |
| 2003/0043378 | A1 | 3/2003 | DiDomenico et al. |
| 2013/0039811 | A1 | 2/2013 | Zochbauer et al. |
| 2013/0301051 | A1* | 11/2013 | Pogosyan ................. G01J 1/08 250/578.1 |
| 2014/0361171 | A1* | 12/2014 | Disch ...................... G01J 3/427 250/338.5 |
| 2015/0124429 | A1* | 5/2015 | Hoehmann ............. F21V 17/02 362/84 |
| 2018/0011007 | A1 | 1/2018 | Lindner |

FOREIGN PATENT DOCUMENTS

| | | |
|---|---|---|
| DE | 202016106260 U1 | 2/2018 |
| EP | 0193718 A1 | 9/1986 |
| EP | 2472249 A1 | 7/2012 |
| EP | 3321658 A1 | 5/2018 |
| JP | H05332933 A | 12/1993 |
| JP | 5349996 B2 | 11/2013 |
| WO | 2003019160 A2 | 3/2003 |
| WO | 2005100613 A2 | 10/2005 |

* cited by examiner

IN-SITU INFRA-RED AND ULTRA-VIOLET PHOTOMETER

TECHNICAL FIELD

The invention relates to gas monitoring/analysis techniques, and more particularly to an improved in-situ photometer with combined Infra-Red (IR) and Ultra Violet (UV) measurement, and to a method for analysing the composition of a sample gas.

BACKGROUND

A gas stream may be required to be analysed to determine the species and concentrations of gases therein. Gas analysis is typically required for exhaust gases in applications such as power generation, incineration, shipping, steel production, etc. Such industries are under increasing pressure from environmental legislation to reduce pollution levels, which is driving a reduction in the monitoring ranges for gaseous emissions and a requirement for greater accuracy/sensitivity of measurement devices.

It is known to provide a prior art Infra-Red (IR) photometer that is located in-situ in an exhaust stack (i.e. chimney) to monitor gaseous pollutant emissions. Such a system may be termed an in-situ Continuous Emission Monitoring System (CEMS). A known CEMS can utilise up to eight wavelengths of light to monitor up to six different gases within the exhaust stream, whereby the wavelength used for monitoring is dependent on the gases to be detected. For specific gases the CEMS may also use the known Gas Filter Correlation (GFC) technique.

An example of the known prior art in-situ IR photometer is shown in FIG. 1 (Prior Art), generally designated 8. A sampling probe 10 is shown which is inserted in an exhaust stack (not shown) up to a flange 12 such that a body 14 of the photometer is on an outside of the exhaust stack. A sampling cell 16 is provided in the probe 10 which comprises a sintered assembly. A lens 18 is also shown in the probe 10. An IR source 20 is provided in the body 14 which transmits IR light to exhaust gas in the gas cell 16. The IR light passes through one of eight filters provided on a filter wheel 22, which is selected under the control of a motor 24. After the IR light has passed through the gas sample and back it impinges on an IR detector 26. This known photometer 8 is a multi-component device that uses eight wavelengths, typically using two wavelengths for each gas (reference and measure) and therefore working on the principle of "dual wavelength single beam" detection.

A problem with the known in-situ CEMS is that the limit of performance to measure gaseous emissions over a smaller monitoring range has been reached. This may be a particular problem with a marine Exhaust Gas Cleaning System (EGCS), where the measurement of exhaust stack gases is difficult to achieve after the exhaust gas has been cleaned (e.g. cleaning using sea water Flue Gas Desulfurization (FGD) systems) to remove Sulphur Dioxide ($SO_2$). For example, the known in-situ CEMS typically provides a range measurement for $SO_2$ in the range 0-150 ppm, and a range measurement for $NO_2$ in the range 0-300 ppm, but these ranges are not low enough (i.e. do not provide sufficient accuracy/sensitivity) to meet the latest legislation.

Further, drift in the measurement of gases using photometers is a known problem. To remove drift, two different techniques are known—"single wavelength dual beam" and "dual wavelength single beam". The "single wavelength dual beam" technique uses a common light source and detector, whereby the beam is split into two paths. One path is passed through a sample cell containing the gas sample and the other path is passed through a parallel cell containing air. By comparing the signals from each path, the concentration of a particular gas can be calculated. The "dual wavelength single beam" technique uses a common source and detector, whereby a reference wavelength and a measured wavelength are alternatively sent through the sample cell as a single beam. By comparing the signals from each of the wavelengths, the concentration of a particular gas can be calculated. In general it is considered that the "dual wavelength single beam" is more effective at reducing or avoiding drift that the "single wavelength dual beam".

It is broadly an object of the present invention to address one or more of the above mentioned disadvantages of the previously known apparatus and methods.

SUMMARY

What is required is a photometer and method for analysing the composition of a sample gas, which may reduce or minimise at least some of the above-mentioned problems.

According to a first aspect of the invention, there is provided a photometer for analysing the composition of a sample gas. The photometer comprises an infra-red (IR) source configured to direct a first plurality of pulses of IR radiation through the sample gas to an IR detector. The photometer further comprises an ultraviolet (UV) source configured to generate a second plurality of pulses of UV radiation for conveyance to a UV detector. A path selection arrangement configured to selectively convey different ones of the second plurality of pulses through the sample gas and to the UV detector. The photometer further comprises processing circuitry coupled to the IR source, the UV source, the IR detector, the UV detector and the path selection arrangement. The processing circuitry is configured to (i) select the wavelength to be used for a given UV pulse of the second plurality of pulses, (ii) receive a plurality of detection signals from each of the IR detector and the UV detector and (iii) based on the detection signals, determine a concentration of at least one component of the sample gas.

Such an apparatus provides the advantage that, at least in embodiments, using UV monitoring to measure $SO_2$ significantly improves the performance of the in-situ IR photometer in terms of range measurement. For example, the in-situ CEMS of the invention typically provides an improved range measurement for $SO_2$ in the range 0-30 ppm, and a range measurement for $NO_2$ in the range 0-30 ppm. The advantages provided by the UV diode include being able to use the in-situ IR photometer in the marine industry to measure and analyse exhaust stack gases after being cleaned by the known marine Exhaust Gas Cleaning Systems using sea water Flue Gas Desulfurization. Such an improved in-situ infra-red photometer may also improve the capability of the apparatus in land based FGD applications for $SO_2$ monitoring, or land based Selective Catalytic Reduction (SCR) applications for $NO_2$ monitoring. It will be appreciated that for item (iii) above the determination of the concentration of at least one component of the sample gas is based on the level (i.e. amplitude, intensity, or magnitude) of the detection signals.

Preferably at least two of the first plurality of pulses are of different wavelength. Preferably at least two of the second plurality of pulses are of different wavelength. Such arrangements provide a reference and a measure wavelength, and have the advantage of an improved stability of the measured signal as per the "dual wavelength single beam" detection technique.

Preferably the path selection arrangement includes a rotating member, the rotating member having at least one annular inner slot and at least one annular outer slot, the inner slot and outer slot being at radially different positions. Preferably the path selection arrangement includes a conveyance post having a first port and a second port, whereby conveyance of UV radiation from the UV source to the first port and the second port is enabled when the inner slot and the outer slot overlap with the first port and the second port, respectively. Preferably the path selection arrangement further includes a first light path coupling the first port to a transmitter part of a light transmitter/receiver module, for directing the UV pulse to the sample gas. Preferably the path selection arrangement further includes a second light path coupling a receiver part of the light transmitter/receiver module to the UV detector. Preferably the path selection arrangement further includes a third light path coupling the second port direct to the UV detector.

In one embodiment, the first light path, the second light path and/or the third light path comprise light guides. Preferably at least one of the light guides is an optical fibre.

Preferably the processing circuitry is configured to control the timing of the pulses of the second plurality of pulses and select the wavelength to be used for a given UV pulse of the second plurality, whereby successive pulses through the first port and/or successive pulses through the second port are of different wavelengths.

In one embodiment, the processing circuitry is configured to control the timing of the pulses of the second plurality of pulses and/or select the wavelength to be used for a given UV pulse of the second plurality, whereby the plurality of detection signals received by the UV detector include: (i) a reference reading, corresponding to a path of UV radiation direct from the UV source to the UV detector, (ii) a dark reading, corresponding to the sample gas not being illuminated by UV radiation, and/or (iii) a measurement reading, corresponding to a path of UV radiation from the UV source to the UV detector via the sample gas.

Preferably the measurement reading corresponds to the inner slot overlapping with the first port, the reference reading corresponds to the outer slot overlapping with the second port, and/or the dark reading corresponds to no overlapping of the slots and ports.

In one embodiment, the path selection arrangement includes at least one pair of inner slots and/or at least one pair of outer slots. Preferably, for a given pair, the inner slots and/or outer slots are spaced apart around the rotating member. Preferably, for a given pair, the inner slots and/or outer slots are diametrically opposed.

In one embodiment, the rotating member includes thereon a plurality of timing indicia and wherein the processing circuitry is configured to (i) detect, during rotation of the rotating member, the passing of the indicia past an indicium detector; and (ii) determine the angular position of the inner slots and/or outer slots based on the detected passing of indicia. Preferably the timing indicia include a primary indicium and a plurality of secondary indicia. Preferably the timing indicia comprise a plurality of through holes or cut-outs angularly spaced apart around the rotating member. Preferably the timing indicia comprise a plurality of through holes or cut-outs equally angularly spaced apart around the rotating member. Preferably the timing indicia comprise cut-outs disposed at the periphery of the rotating member.

Preferably the primary indicium is larger than the secondary indicia. Preferably the indicium detector comprises an optical transmitter/receiver.

Preferably the rotating member comprises a filter wheel having a plurality of filter elements spaced apart around the filter wheel; wherein the filter elements are disposed at a different radial position to the inner slots and/or outer slots.

According to another aspect of the invention there is provided a method of analysing the composition of a sample gas. The method comprises providing a photometer according to any of the claims. The method further comprises operating the processing circuitry to (i) receive a plurality of detection signals from each of the IR detector and the UV detector and (ii) based on the detection signals, determine a concentration of at least one component of the sample gas.

Preferably the method further includes operating the processing circuitry to select the wavelength to be used for a given UV pulse of the second plurality of pulses.

According to an alternative characterisation of the invention there is provided a photometer for analysing the composition of a sample gas, the photometer comprising: an infra-red (IR) source configured to direct a first plurality of pulses of IR radiation through the sample gas in a sample cell to an IR detector; an ultraviolet (UV) source configured to direct a second plurality of pulses of UV radiation through the sample gas to a UV detector; and processing circuitry coupled to the IR source, the UV source, the IR detector and the UV detector, the processing circuitry being configured to (i) receive a plurality of detection signals from each of the IR detector and the UV detector and (ii) based on the detection signals, determine a concentration of at least one component of the sample gas.

According to an alternative characterisation of the invention there is provided a photometer for analysing the composition of a sample gas, the photometer comprising: an infra-red (IR) source configured to direct a first plurality of pulses of IR radiation through the sample gas to an IR detector; an ultraviolet (UV) source configured to direct a second plurality of pulses of UV radiation through the sample gas to a UV detector; and processing circuitry coupled to the IR source, the UV source, the IR detector and the UV detector, the processing circuitry being configured to (i) receive a plurality of detection signals from each of the IR detector and the UV detector and (ii) based on the detection signals, determine a concentration of at least one component of the sample gas.

According to an alternative characterisation of the invention there is provided a photometer for analysing the composition of a sample gas, the photometer comprising: an infra-red (IR) source configured to direct a first plurality of pulses of IR radiation through the sample gas to an IR detector; an ultraviolet (UV) source configured to direct a second plurality of pulses of UV radiation through the sample gas to a UV detector; and processing circuitry coupled to the IR source, the UV source, the IR detector and the UV detector, the processing circuitry being configured to (i) receive a plurality of detection signals from each of the IR detector and the UV detector, (ii) determine a first concentration of a first component of the sample gas using detection signals from the IR detector, (iii) determine a second concentration of a second component of the sample gas using detection signals from the UV detector, and (iv) based on the detection signals, determine a corrected concentration of the second component, the corrected concentration being the second concentration corrected for cross-sensitivity based on the first concentration.

Any preferred or optional features of one aspect or characterisation of the invention may be a preferred or optional feature of other aspects or characterisations of the invention.

BRIEF DESCRIPTION OF THE DRAWINGS

Other features of the invention will be apparent from the following description of preferred embodiments shown by way of example only with reference to the accompanying drawings, in which.

DETAILED DESCRIPTION

Figure 1:
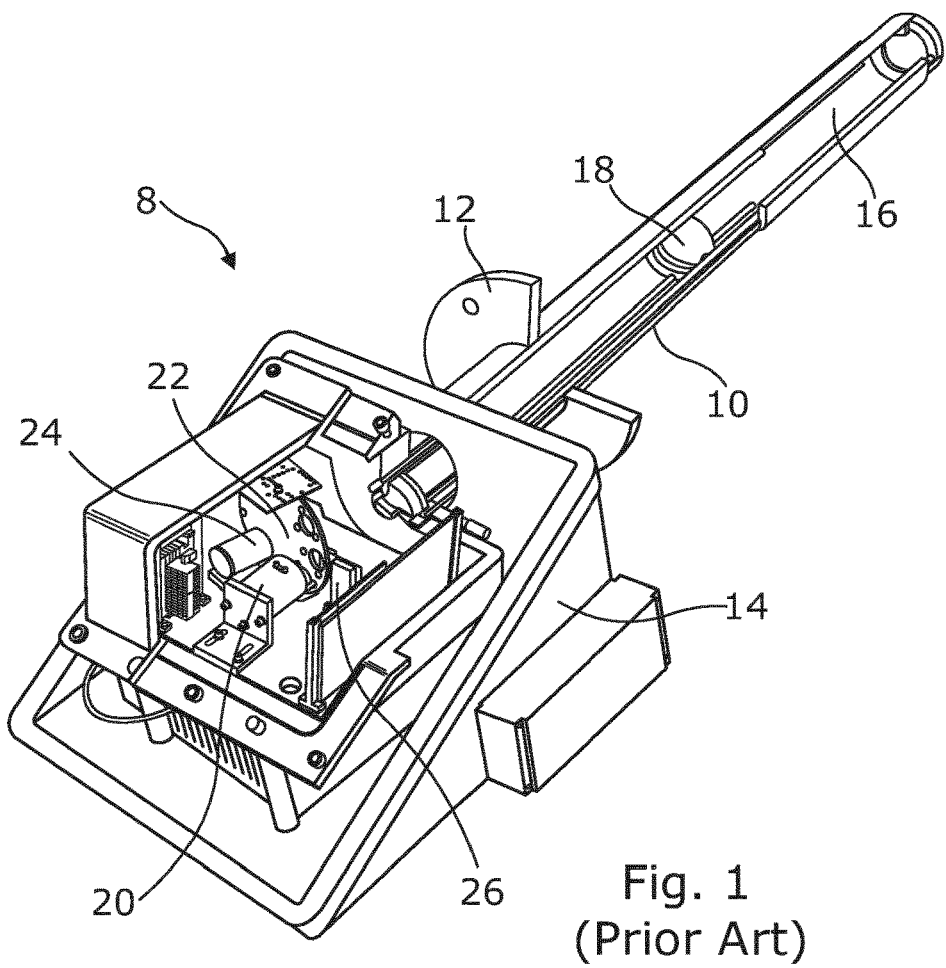
FIG. 1 (PRIOR ART) shows a known form of gas photometer.
Figure 2:
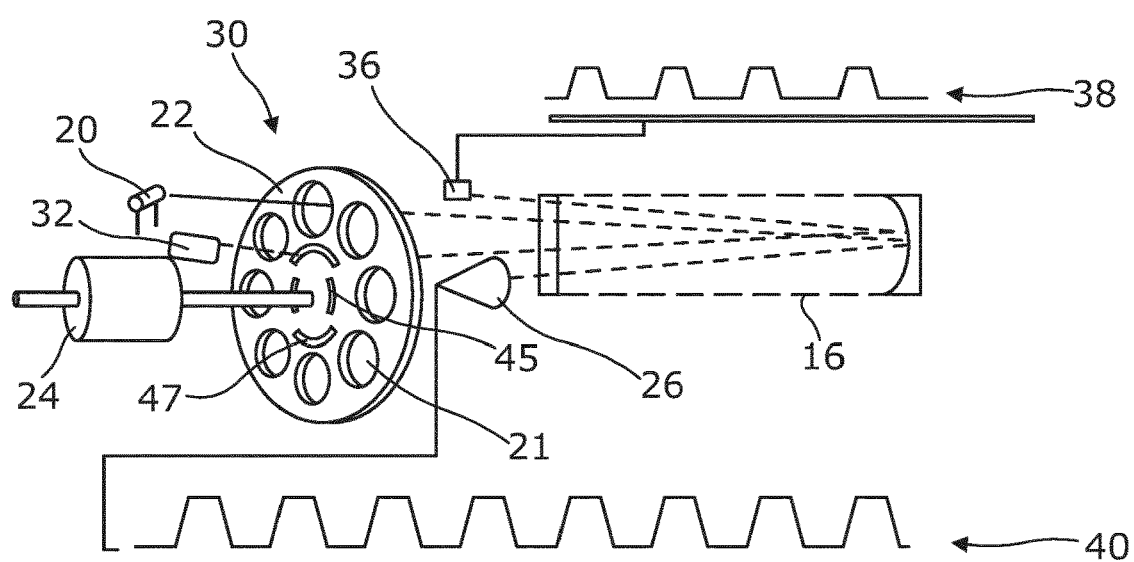
FIG. 2 is a perspective view of a photometer according to an embodiment of the invention.
Figure 3:
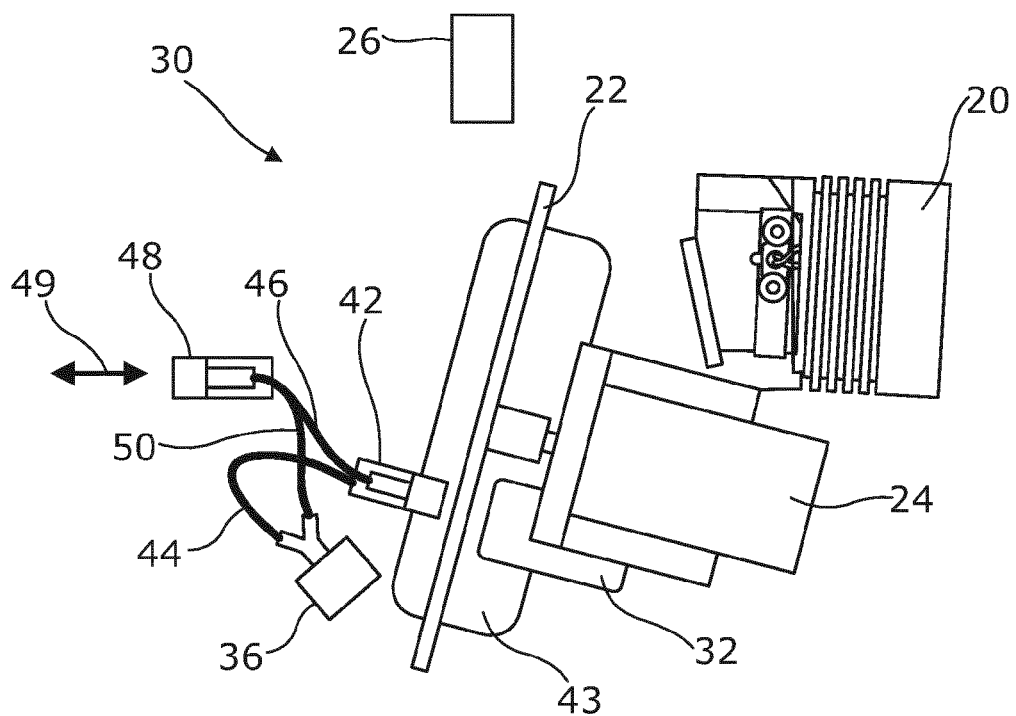
FIG. 3 is an enlarged view of a path selection arrangement using in the photometer of FIG. 2.
Figure 4:
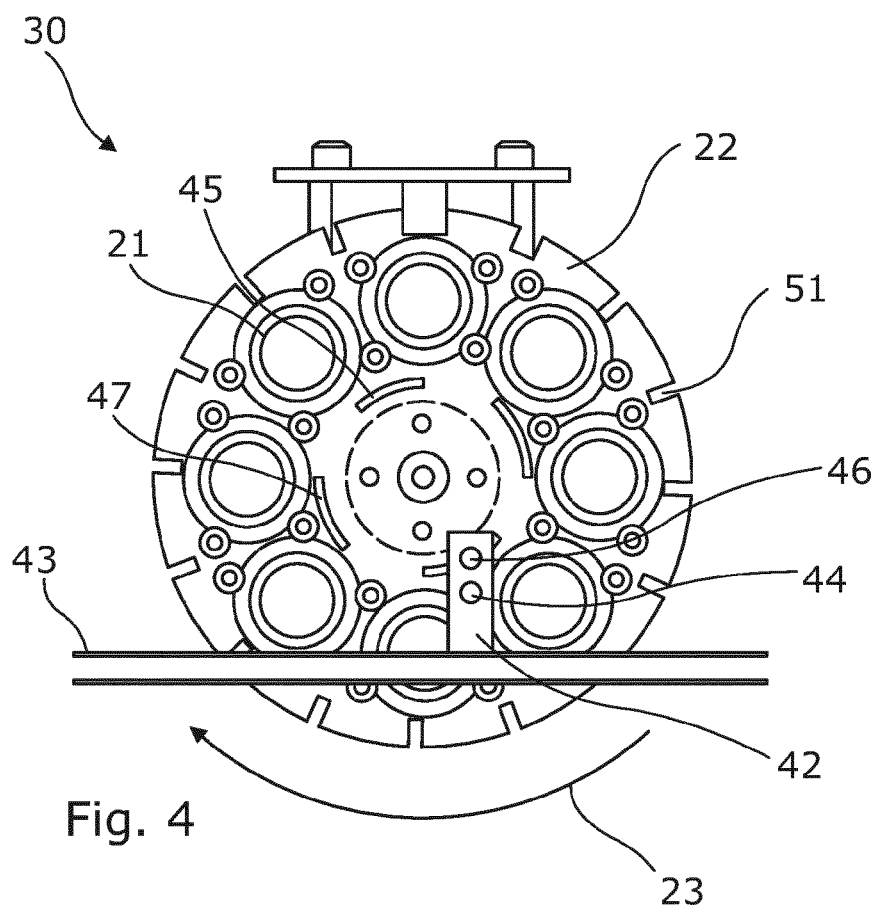
FIG. 4 is an axial view of the path selection arrangement of FIG. 3.

FIGS. 2, 3 and 4 show an improved in-situ Infra-Red (IR) photometer with combined IR and Ultra Violet (UV) measurement according to an embodiment of the invention, generally designated 30. In FIGS. 2 to 4 like features to the prior art arrangement of FIG. 1 are shown with like reference numerals. In FIGS. 2 and 3 a UV source 32 (e.g. a UV light emitting diode) is provided in the body 14 which transmits UV light to exhaust gas in the gas cell 16 through one of two light slots 45, 47, which are at different radial positions in the filter wheel 22. The two light slots 45, 47 are through-holes in the filter wheel 22, and are part-circular (i.e. arcuate) and elongate. After the UV light has passed through the gas sample and back it impinges on a UV detector 36. Also shown in FIG. 2 is a UV signal 38 produced from the UV detector, and JR signal 40 produced from the IR detector 26. Also shown are the eight filters 21 of the filter wheel 22 for selecting one of the eight wavelengths as described above using the JR source 20.

As shown in FIGS. 3 and 4 the UV source 32 alternatively illuminates the two pairs of slots 45, 47 as the filter wheel 22 rotates, shown at 23. The UV light passes through the two pairs of slots 45, 47 and is then input to the two optic fibres 44, 46 which are connected to a pillar 42, which is mounted on a support 43. After passing through the spinning filter wheel 22 the UV light illuminates the two optic fibres 44, 46 in turn. As shown in FIG. 4 the pillar 42 provides the optic fibre entry point for the optic fibres 44, 46 one above the other so that one UV light beam is provided via the optic fibre 44 to the detector 36, and the other UV light beam is provided via the optic fibre 46 to a transmitter/receiver module 48. FIG. 4 shows the arrangement of the filter wheel 22 relative to the pillar 42 for the optic fibres 44, 46. Also shown in FIG. 4 are the two light slots 45 on the filter wheel 22, which are diametrically opposed to each other and offset from the two light slots 47 on the filter wheel 22 which are also diametrically opposed to each other. The light slot 45 is to provide the UV beams to the UV detector 36 via the optic fibre 44, and the light slots 47 is for the UV beam to the transmitter/receiver module 48. The transmitter/receiver module 48 is a lens pillar module and operates to transmit UV light from the optic fibre 46 through the gas sample in the gas cell 16, and to receive reflected UV light from the gas sample in the gas cell 16 (as shown by the double headed arrow 49) and to pass it to the detector 36 via an optic fibre 50.

As the motor 24 rotates the filter wheel 22 the two light slots 45, 47 for the UV light provide the possibility of using two UV light beams, which are alternatively switched. The UV source 32 is for $SO_2$ monitoring and operates at a wavelength of 250 nm to 325 nm (and may be centred around 280 nm) in a dual path configuration, which meets the requirement of using a single source and detector as required for the "dual wavelength single beam" technique mentioned above.

The UV source 32 contains two UV diodes that sequentially switch and operate at different wavelengths (one to monitor $SO_2$ operating between 250 nm to 325 nm the other to monitor $NO_2$ operating between 350 nm to 450 nm). Such an arrangement for UV monitoring combined with the IR capabilities permits two gases (i.e. $SO_2$ and $NO_2$) to be monitored, and also provides the advantage that lower $NO_2$ concentrations can be monitored.

The data from each of the UV and IR systems is also used to correct for cross sensitivity (i.e. water vapour effect on the $NO_2$). This is achieved by monitoring the $NO_2$ in the UV signal and correcting for any cross sensitivity using the IR range for $H_2O$. In this manner the UV and IR capabilities are combined to produce an improved monitoring compared to ether the UV or IR capability when used alone.

The signal processing of the UV signal 38 and IR signal 40 is carried out on an analyser PCB (not shown), which utilises the existing sixteen timing slots 51 on the circumference of the filter wheel 22 to determine the position of the UV light slots 45, 47 with respect to the UV source(s). Using the arrangements shown in FIGS. 2 to 4 the UV beam from the UV source 32 is alternatively sent through the sample cell 16 and directly to the detector 36. With such an arrangement any drift caused by either the UV detector 36 or the UV source 32 can be removed. This is achieved by the two off-set slots 45, 47 in the filter wheel 22 whereby one slot 45 is aligned with the fibre 46 to the gas cell 16, and the other slot 47 is aligned with the fibre 44 to the UV detector 36. It will be appreciated that UV pulses are alternatively sent to the UV detector 36 via the gas cell 16 (i.e. fibre 46 out, fibre 50 return), and directly to the UV detector 36 (i.e. via the fibre 44). The timing and switching of the UV beams are achieved by using the filter wheel 22 with the slots 45, 47 to provide a reference reading, a dark reading, and a measure reading. All signals are combine electronically using a microprocessor device (not shown) to provide measurement readings as required on a display (not shown) which may be in the form of a graph of as numerical values.

It will be appreciated that whereas the use of optic fibre 44, 46, 50 is described above, in an alternative arrangement other types of waveguide or light guides may be used to achieve the dual UV paths. It will also be appreciated that the filter wheel 22 continuously rotates as shown at 23 when performing both UV and IR monitoring.

Figure 5:
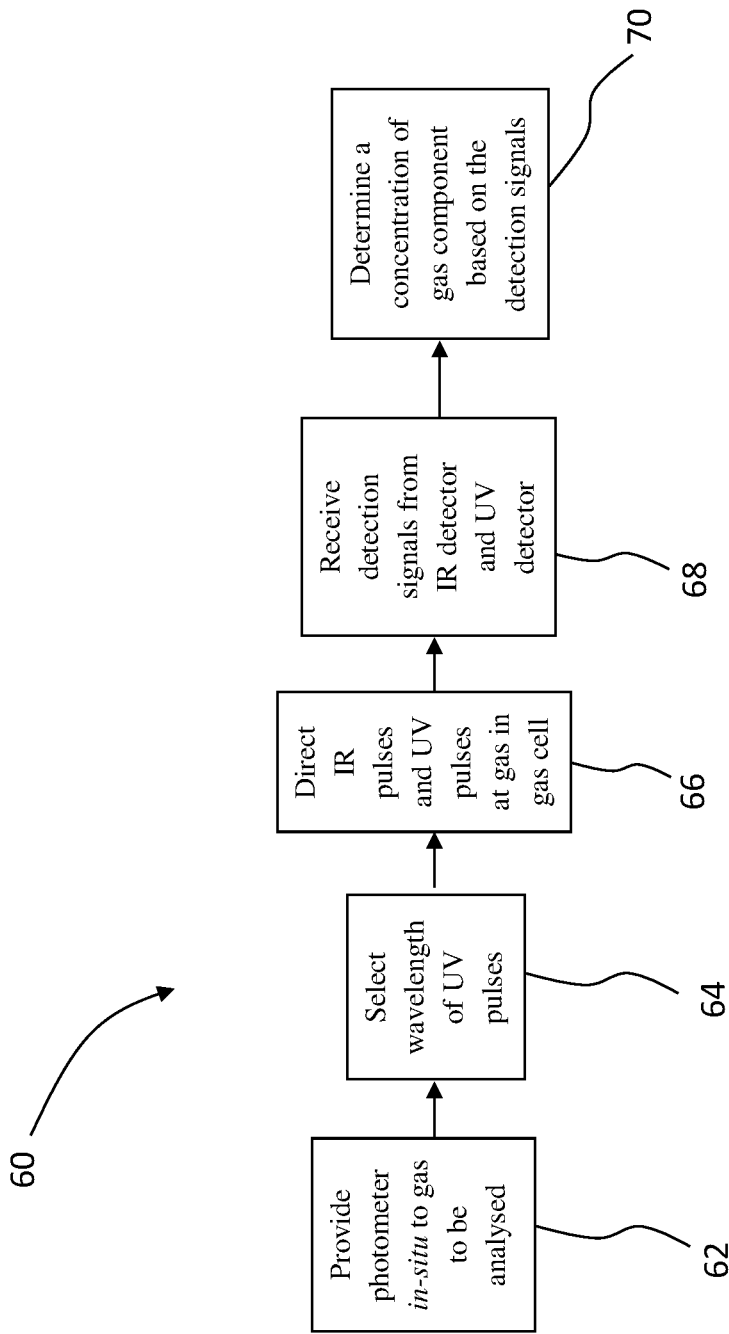
FIG. 5 shows a method according to an embodiment of the invention.

FIG. 5 shows steps of a method according to an embodiment of the invention, generally designated 60. It will be appreciated that the steps may be performed in a different order, and may not necessarily be performed in the order shown in FIG. 5.

Firstly, a photometer is provided (block 62) in-situ where the gas is to be analysed, for example as in the measurement scenarios mentioned hereinabove. Processing circuitry (e.g. the above-mentioned analyser PCB (not shown)) controls the timing and wavelength of pulses, and the method proceeds with the processing circuitry selecting (block 64) the wavelength of a given UV pulse (i.e. the measure and reference UV pulses), using the aforementioned timing mechanisms. In one arrangement the UV wavelengths are dynamically selected. Next, the IR pulses from the IR source and the UV pulses from the UV source are directed (block 66) at the sample gas in gas cell. Using the IR detector and UV detector, detection signals are received (block 68). Finally, the processing circuitry determines (block 70) a concentration of gas component of the sample gas based on the detection signals.

The arrangements described herein provide a photometer with a sufficiently acceptable performance in terms of drift and noise, and also permit the use of UV and IR measurement in a combined unit with only one sampling cell 16. It will be appreciated that whereas the UV diode 32 operates at a narrow fixed wavelength, the combination with IR measurement permits the apparatus to be used with the conventional "dual beam" principle in an "in-situ" gas analyser and over a broader wavelength range. In summary, embodiments of the invention provide:
1. Combined UV and IR optical system with combined UV and IR timing system;
2. Combined UV and IR measurement in the same sample cell;
3. Combined signal processing of the UV and IR signals; and
4. Combined cross sensitivity corrections.

Furthermore, the improved in-situ IR photometer provides an additional range capability (i.e. two additional UV channels), which increase the prior art system from 6 to 8 channels. In addition the improved in-situ IR photometer releases IR wavelengths, which reduces compromises on gas measurement for certain applications. A major limitation of the prior art apparatus of FIG. 1 is that there are only 8 wavelengths available so when monitoring 6 gas species it is necessary to make compromises on the wavelengths allocated to each gas depending on the gases to be monitored. When monitoring NO and CO (using GFC) and $SO_2$ (using a Measure Filter & Wide Band Filter method), which takes up two wavelength slots each, then for cross sensitivity correction it is necessary to monitor $CO_2$ & $H_2O$. Using the prior art apparatus of FIG. 1, as there are only two slots left it is necessary to use a fixed reference number for $CO_2$ & $H_2O$ which is not ideal and can compromise the accuracy of the measurement. When using the prior art apparatus of FIG. 1 a measure filter is often used for one gas as a reference filter for a second gas, which adds significantly to calibration time and accuracy of the measurement. Using embodiments of the invention shown in FIGS. 2 to 4, the inclusion of a UV $SO_2$ channel frees up two filter slots for IR ranges. Such an arrangement provides additional operational flexibility for the apparatus of the invention, and also improves the cross sensitivity correction for gas monitoring.

The invention claimed is:

1. A photometer for analyzing the composition of a sample gas, the photometer comprising:
    an infra-red (IR) source configured to direct a first plurality of pulses of IR radiation through the sample gas to an IR detector;
    an ultraviolet (UV) source configured to generate a second plurality of pulses of UV radiation for conveyance to a UV detector;
    a path selection arrangement configured to selectively convey different ones of the second plurality of pulses through the sample gas and to the UV detector; and
    processing circuitry coupled to the IR source, the UV source, the IR detector, the UV detector and the path selection arrangement, the processing circuitry being configured to (i) select a wavelength to be used for a given UV pulse of the second plurality of pulses, (ii) receive a plurality of detection signals from each of the IR detector and the UV detector and (iii) based on the detection signals, determine a concentration of at least one component of the sample gas;
    wherein the path selection arrangement includes a rotating member, the rotating member having at least one annular inner slot and at least one annular outer slot, the inner slot and outer slot being at radially different positions; and
    wherein the rotating member includes thereon a plurality of timing indicia and wherein the processing circuitry is configured to: (i) detect, during rotation of the rotating member, a passing of the timing indicia past an indicium detector; and (ii) determine an angular position of the inner slots and/or outer slots based on the passing of the timing indicia.

2. The photometer according to claim 1, wherein at least two of the first plurality of pulses are of different wavelength.

3. The photometer according to claim 1, wherein at least two of the second plurality of pulses are of different wavelength.

4. The photometer according to claim 1, wherein the path selection arrangement includes a pillar having a first port and a second port, whereby conveyance of UV radiation from the UV source to the first port and the second port is enabled when the inner slot and the outer slot overlap with the first port and the second port, respectively.

5. The photometer according to claim 4, wherein the path selection arrangement further includes a first light path coupling the first port to a transmitter part of a light transmitter/receiver module, for directing the given UV pulse to the sample gas.

6. The photometer according to claim 5, wherein the path selection arrangement further includes a second light path coupling a receiver part of the light transmitter/receiver module to the UV detector.

7. The photometer according to claim 6, wherein the path selection arrangement further includes a third light path coupling the second port directly to the UV detector.

8. The photometer according to claim 7, wherein the first light path, the second light path and/or the third light path comprise light guides.

9. The photometer according to claim 8, wherein at least one of the light guides is an optical fibre.

10. The photometer according to claim 4, wherein the processing circuitry is further configured to control a timing of the pulses of the second plurality of pulses, whereby successive pulses through one or both of the first and second ports are of different wavelengths.

11. The photometer according to claim 1, wherein the processing circuitry is further configured to control a timing of the pulses of the second plurality of pulses, whereby the plurality of detection signals received by the UV detector include:
    (i) a reference reading, corresponding to a path of UV radiation direct from the UV source to the UV detector,
    (ii) a dark reading, corresponding to the sample gas not being illuminated by UV radiation, and/or
    (iii) a measurement reading, corresponding to a path of UV radiation from the UV source to the UV detector via the sample gas.

12. The photometer according to claim 11, wherein the path selection arrangement includes:

a rotating member, the rotating member having at least one annular inner slot and at least one annular outer slot, the inner slot and outer slot being at radially different positions; and a pillar having a first port and a second port, whereby conveyance of UV radiation from the UV source to the first port and the second port is enabled when the inner slot and the outer slot overlap with the first port and the second port, respectively, wherein the measurement reading corresponds to the inner slot overlapping with the first port, the reference reading corresponds to the outer slot overlapping with the second port, and/or the dark reading corresponds to no overlapping of the slots and ports.

13. The photometer according to claim 1, wherein the path selection arrangement includes at least one pair of inner slots and/or at least one pair of outer slots.

14. The photometer according to claim 13, wherein, for a given pair, the inner slots and/or outer slots are spaced apart around the rotating member.

15. The photometer according to claim 13, wherein, for a given pair, the inner slots and/or outer slots are diametrically opposed.

16. The photometer according to claim 1, wherein the rotating member comprises a filter wheel having a plurality of filter elements spaced apart around the filter wheel; wherein the filter elements are disposed at a different radial position to the inner slots and/or outer slots.

17. A method of analyzing the composition of a sample gas, the method comprising the steps of:

providing a photometer comprising an infra-red (IR) source configured to direct a first plurality of pulses of IR radiation through the sample gas to an IR detector, an ultraviolet (UV) source configured to generate a second plurality of pulses of UV radiation for conveyance to a UV detector, a path selection arrangement configured to selectively convey different ones of the second plurality of pulses through the sample gas and to the UV detector, and processing circuitry coupled to the IR source, the UV source, the IR detector, the UV detector and the path selection arrangement, wherein the path selection arrangement includes a rotating member, the rotating member having at least one annular inner slot and at least one annular outer slot, the inner slot and outer slot being at radially different positions, and wherein the rotating member includes thereon a plurality of timing indicia;

operating the processing circuitry to (i) receive a plurality of detection signals from each of the IR detector and the UV detector, (ii) detect, during rotation of the rotating member, a passing of the timing indicia past an indicium detector, and (iii) determine an angular position of the inner slots and/or outer slots based on the passing of the timing indicia; and determining a concentration of at least one component of the sample gas based on the detection signals.

18. The method according to claim 17, further comprising the step of operating the processing circuitry to select a wavelength to be used for a given UV pulse of the second plurality of pulses.

* * * * *